United States Patent [19]
Phillips

[11] Patent Number: 4,678,809
[45] Date of Patent: Jul. 7, 1987

[54] INJECTABLE FOMULATIONS OF DISULFIRAM FOR THE TREATMENT OF ALCOHOLISM

[76] Inventor: Michael Phillips, 1740 Hinman Ave., Apt. 3B, Evanston, Ill. 60201

[21] Appl. No.: 697,103

[22] Filed: Feb. 1, 1985

[51] Int. Cl.$^4$ .................. A61K 31/16; A61K 9/22; A61K 9/30; A61K 9/32
[52] U.S. Cl. ...................... 514/599; 424/78; 424/486
[58] Field of Search .......... 424/78, 19, 31, 32, 424/33; 514/599

[56] References Cited
PUBLICATIONS

Bergstrom et al Lancet, 1: 49–50, 1982.
Chem Abst., 86: 127,227k 1977.
Chem Abst., 91: 62662e, 1979.
Chem Abst. 92: 203,452w 1980.
Chem Abst., 92: 105587z, 1980.
Chem. Absts., 102: 172533s, 1985.

Primary Examiner—Johnnie R. Brown
Assistant Examiner—John W. Rollins, Jr.
Attorney, Agent, or Firm—Kane, Dalsimer, Kane, Sullivan and Kurucz

[57] ABSTRACT

The disclosure is of the use of an injectable formulation of disulfiram for the treatment of alcoholism. One formulation comprises disulfiram and a biodegradable polymer. Another formulation comprises a slurry of disulfiram in normal saline. After injection, disulfiram is released from the injection site in a sustained-release manner.

2 Claims, 6 Drawing Figures

INJECTABLE FOMULATIONS OF DISULFIRAM FOR THE TREATMENT OF ALCOHOLISM

BACKGROUND OF THE INVENTION

1. Field of the Invention

The present invention concerns an improved injectable formulation of the drug disulfiram, for use in the treatment of alcoholism.

2. Brief Description of the Prior Art

Disulfiram (DSF) is a drug widely used in the treatment of alcoholism. Anyone who consumes ethyl alcohol after pretreatment with DSF (taken orally) will experience the subjectively unpleasant Disulfiram-Ethanol Reaction (DER) characterized by nausea, palpitations, flushing, hyperventilation and hypotension. In theory, treatment of an alcoholic patient with DSF should discourage a relapse into impulsive drinking. In practice, DSF therapy often ends in failure when the patient stops taking the drug and resumes drinking after the effects have worn off. An alternative approach, parenteral therapy with subcutaneous implants of sterile DSF tablets has been widely practiced for many years but it is now clear that these implants are inactive placebos which can not elicit a true DER in alcoholic humans. Alcoholics implanted with DSF tablets do not experience a DER after drinking alcohol, nor do they drink significantly less alcohol than those implanted with an inactive placebo. These failures of therapy are probably due to subtherapeutic dosage as well as the poor bioavailability of DSF tablets in the subcutaneous milieu where they often become encapsulated by fibrotic tissue. The following references describe relevant prior art methods: Bergstrom et al., Lancet 1:49–50, 1982; Kline and Kingstone, Can Med Assoc. J. 116:1382–1383, 1977; Lewis et al., Can Psychiatr. Assoc J. 20:283–286, 1975.

Detoxification of an alcoholic induces a remission of the disease which may be followed by an acute relapse into abusive drinking at any time; treatment with an effective sustained-release formulation of DSF is likely to prolong the duration of the initial remission and lengthen the period between subsequent relapses.

The present invention relates to an effective injectable formulation of DSF wherein the drug is released in a sustained manner over a period of several weeks.

SUMMARY OF THE INVENTION

The present invention comprises a method of treating alcoholic subjects with injectable formulations of disulfiram (DSF). Oral DSF has been widely used for the treatment of alcoholism. It is now possible for the first time to treat alcoholics successfully with injected DSF, without requiring the subject to take a tablet every day, because the injected DSF is released into the circulation in a steady fashion over a long period of time. An alcoholic thus treated would then respond to consumption of alcohol with a variety of unpleasant reactions, including flushing of the face, shortness of breath, dizziness, headaches and blurred vision, and would therefore be motivated to abstain from drinking.

One injectable formulation comprises DSF and a biodegradable polymer. Another formulation comprises DSF in a slurry, suspended in normal saline. Both formulations may be sterilized by gamma irradiation. Both formulations are effective in animals. The formulation of DSF in a slurry, suspended in normal saline, is effective in human subjects.

DETAILED DESCRIPTION OF THE INVENTION

The drug disulfiram (DSF) acts by inactivating aldehyde dehydrogenase, a heterogenous hepatic enzyme responsible for breaking down acetaldehyde produced by the oxidation of ethanol:

If alcohol is consumed after pre-treatment with DSF, acetaldehyde accumulates in the blood, causing a number of unpleasant symptoms such as flushing, palpitations, nausea and hyperventilation. DSF inactivates aldehyde dehydrogenase by irreversible disulfide interchange reactions with thiol groups, and also inhibits dopamine beta hydroxylase, resulting in reduced vasomotor tone and postural hypotension. The typical response to pre-treatment with DSF starts within five to ten minutes of consuming alcohol, ends within 30 minutes, and is followed by a period of sleep and complete recovery. See for example, Lundwall et al., J. Nerv. Ment. Dis. 1971, 158:381–394.

DSF is difficult to prepare in a bioavailable parenteral formulation since it is poorly soluble in water. The present invention describes two parenteral preparations of DSF that exhibit effective bioavailability of the drug, with sustained-release properties over a period of time.

One preparation of the injectable formulation of DSF comprises a combination of DSF and a biodegradable polymer. The preferred polymer is poly(lactic-co-glycolic acid), (PLGA), synthesized as described by Wise et al., in "Drug Carriers in Biology and Medicine", Academic Press, 1979:237–70, which reference is herein incorporated. The preferred ratio of PLGA to DSF is 4 to 1. When implanted subcutaneously, PLGA is believed to degrade slowly into its parent monomers—lactic acid and glycolic acid—while continuously releasing any bound drug at a steady rate. In-vivo studies of PLGA combined with contraceptives, narcotic antagonists and antimalarials have shown that these implants can deliver the drug continuously into the circulation for several months at a time (see Wise et al., supra).

An animal study using the DSF-PLGA formulation demonstrated successfully a sustained systemic delivery of disulfiram for a three month period. During that time, the drug was delivered continuously, though fluctuations were observed in the rate of delivery. An ideal implantable drug delivery system would achieve zero-order kinetics: i.e. the rate of delivery would rapidly reach its maximal value, and remain there until the supply of drug was exhausted. However, in clinical practice, even a non-ideal delivery system may achieve a near-ideal pharmacologic effect, provided that the rate of delivery oscillates within a defined "therapeutic window", with upper and lower limits defined as the rates of delivery at which either toxic effects or inadequate clinical response are respectively observed. Consequently, even though fluctuations were observed in the rate of delivery of disulfiram from the composite implant, it is possible that it could provide an acceptable therapeutic effect for a period of several weeks.

Figure 1:
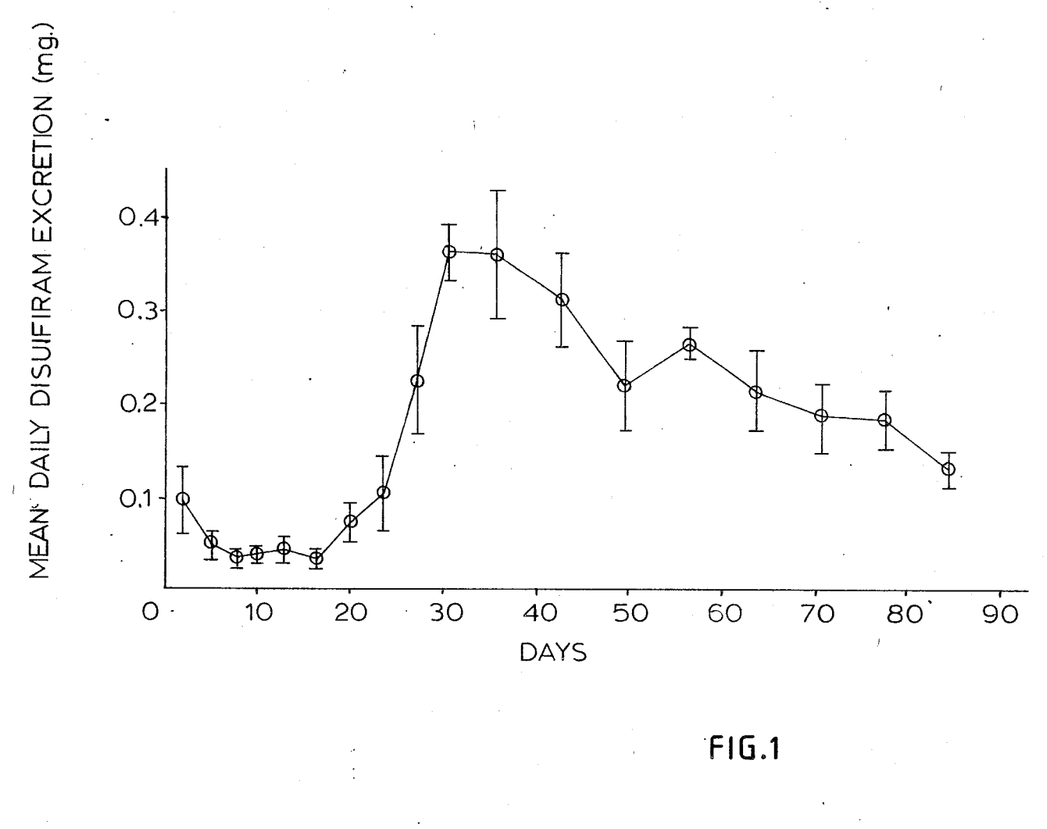
FIG. 1 illustrates the mean daily excretion of radiolabeled metabolites in urine and feces following subcutaneous implantation of the PLGA-disulfiram formulation.
Figure 2:
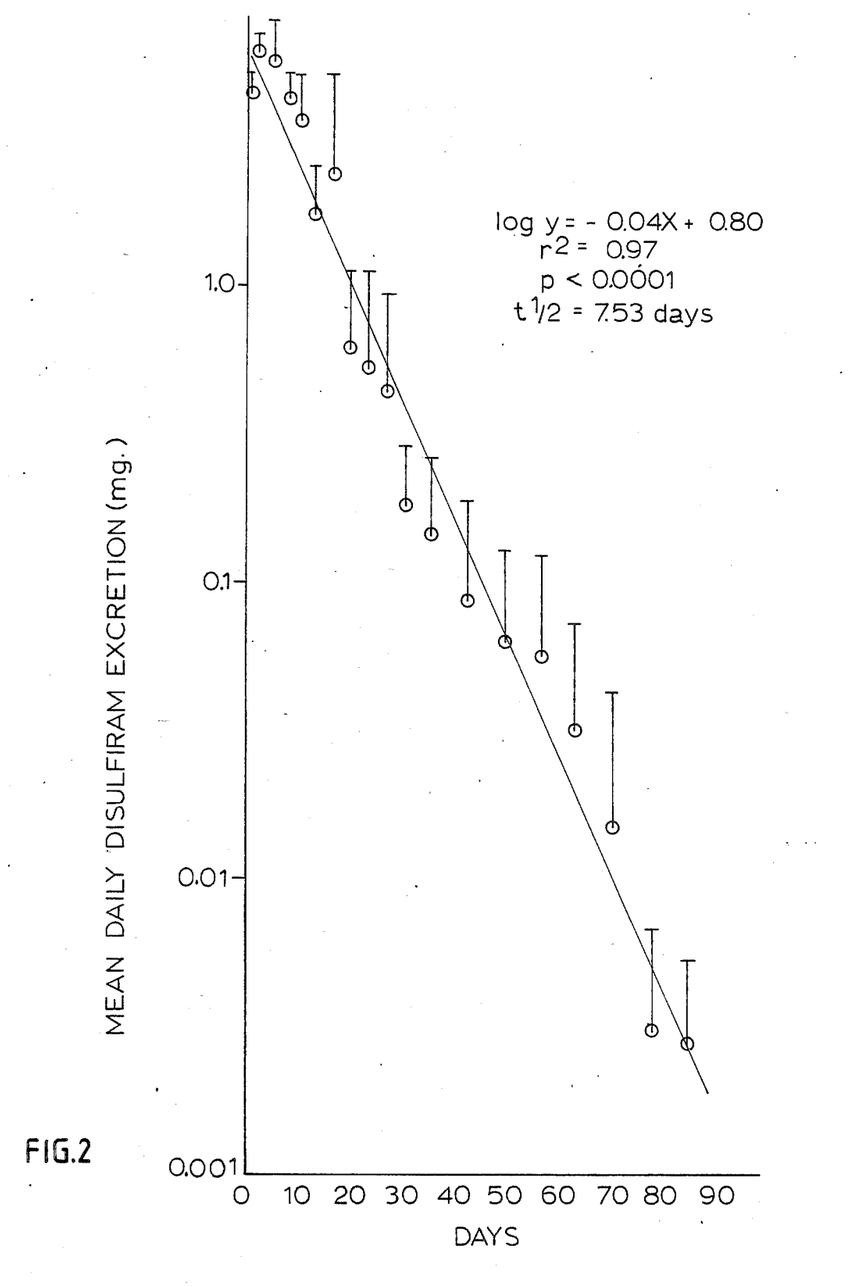
FIG. 2 illustrates the mean daily excretion of radiolabeled metabolites in urine and feces following subcutaneous injection of disulfiram slurry.

The effectiveness of the DSF-PLGA preparation (in an animal study) is shown graphically in FIG. 1. FIG. 2 shows the results of using DSF slurry, also in an animal study. The figures show the mean daily excretion of radiolabeled metabolites in urine and feces following subcutaneous implantation of the formulations. Bars indicate one standard deviation. Example 1 describes in detail the experimental protocol. No evidence of local or systemic toxicity was observed with either DSF-PLGA formulation or with DSF alone in these studies involving subcutaneous implantations in rats.

An alternative preparation of the invention of the injectable formulation of DSF comprises a suspension of DSF in normal saline. The discovery of this formulation is based in part on the observation of the mobilization and bioavailability of disulfiram slurry in the control used in the evaluation of the DSF-PLGA formulation (see FIG. 2). The first-order mobilization kinetics of the injected powdered disulfiram in the control group are consistent with the commonly observed kinetics of other parenterally administered drugs. It is possible that the bioavailability of the disulfiram was enhanced by administering it in powder form, thus greatly increasing the surface area available for the dissolution of drug in the interstitial fluid. The long depot half-life of the powdered disulfiram (7.53 days) may be a function of its poor solubility in water. It is likely that the DSF powder becomes wetted with interstitial fluid to form a slurry, with a very large surface area of drug exposed to the fluid phase (far larger, certainly, than the surface area of a compacted tablet of the same weight of drug). Despite the very low solubility of DSF in water (0.02 G/100 ml), it is likely that the large surface area of the powdered drug facilitates a fairly rapid equilibration between drug in the solid phase and drug in the liquid phase, and this process continues until the reservoir of drug is depleted. The injection of a slurry of DSF in normal saline into human subjects would be expected to show a similar sustained pharmacologic effect over a period of several weeks, with the mobilization half-life of approximately one week.

In order to be suitable for injection, the formulations must be sterile. The sterilization of DSF presents a formidable technical problem: heat sterilization is not practicable due to the low melting point of the drug (70° C.), nor can it be sterilized by Millipore ® filtration due to its near insolubility in water. Gamma irradiation was therefore used as the best available technique. Preparations after irradiation are completely sterile as demonstrated by conventional methods of sterility testing for the presence of microorganisms. Likewise testing for chemical stability of irradiated samples did not demonstrate any reduction in the concentration of disulfiram.

The suspensions of sterile DSF in sterile normal saline may be preserved in a stable form for long periods prior to injection by the addition of a suspending agent, such as e.g., carboxymethylcellulose.

A clinical study of two alcoholic human subjects who received low doses of parenteral injection of DSF-normal saline formulations successfully demonstrated the effectiveness of the drug and the sustained timed release nature of its action. The parenteral DSF injections were well tolerated by both subjects, with no evidence of systemic or local toxicity. Alcohol challenges at weekly intervals, over the course of one month, produced the subjective as well as the objective chemical and physiological changes of the classic disulfiram-ethanol reaction.

Figure 3:
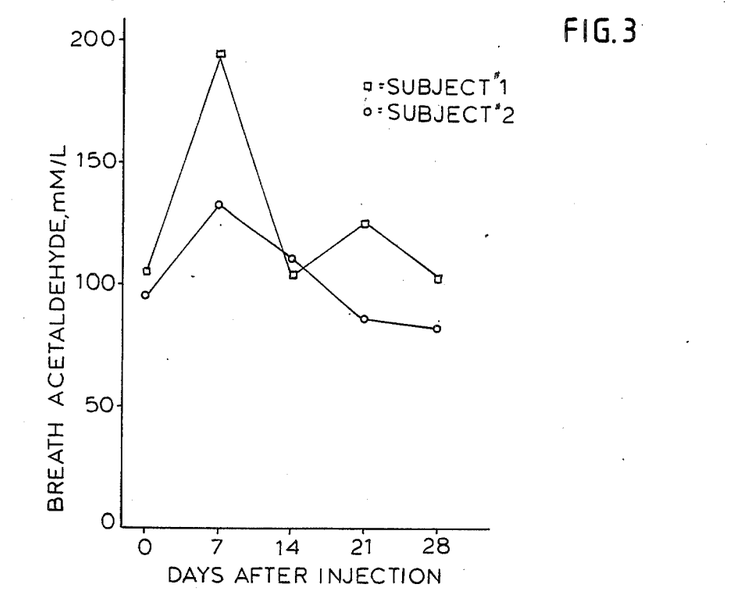
FIG. 3 illustrates the excretion of acetaldehyde in breath following an injection of disulfiram slurry.

Ideally, the concentration of acetaldehyde in the blood is probably the single best objective criterion of the efficacy of the DER. However, blood acetaldehyde levels are notoriously difficult to measure accurately, and are fraught with many sources of experimental error. In order to circumvent these problems, a new technique for collecting breath for assay of ethanol and acetaldehyde has been developed as described by Phillips et al in Alcoholism; Clinical and Experimental Research, 8:293-296, 1984, which reference is herein incorporated. FIG. 3 shows the results of the acetaldehyde assays. It can be seen that the injection of DSF induces elevated levels of acetaldehyde following the comsumption of alcohol. Alcohol challenges yielded positive results in other aspects as well including elevated skin temperatures, dizziness, facial flushing, headache, and blurring of vision; these symptoms are consistent with the classical clinical response to an alcohol challenge after pretreatment with disulfiram.

It is now possible using the injectable formulations of DSF of the present invention, to treat alcoholic subjects over a prolonged period of time. The treatment does not depend on the subject's participation (beyond submitting to an injection), because the subcutaneous implantation of the drug allows it to be released in sustained fashion over a period of time. In animals, a single injection was followed by excretion of DSF over a three month period. In human subjects, a definite clinical response for at least two weeks after injection was demonstrated.

The following examples describe the manner and process of making and using the invention and represent the best mode contemplated by the inventor, but are not to be construed as limiting.

Preparation of Polymer

Poly(lactic-co-glycolic acid)(PLGA)

PLGA was synthesized in bulk in an evacuated glass reaction vessel from a mixture of 90 g L-lactide and 10 g glycolide with 1 g p-toluene sulfonic acid monohydrate as a catalyst. After degassing the mixture to less than 0.05 mm Hg for 45 min, the reaction vessel was sealed, rotated to mix the ingredients, heated at 118° C. for 2 hrs, mixed again, then heated for 10 days at 118°

C.±2° C. The resulting polymer was dissolved in tetrahydrofuran (THF), then filtered through glass wool, precipitated in distilled water and vacuum dried. The mean molecular weight of the PLGA (34,428±877) was determined by dissolving the polymer in THF (5 mg/ml) and assaying by gel-permeation chromatography using a Waters Associates HPLC system equipped with μ-Styragel columns and a differential refractive index detector.

Preparation of Radioactive Injectable Formulation of DSF and Polymer (PLGA)

5.0 mCi radiolabeled disulfiram (tetra(1-14C)-ethylthiuram disulfide) (Amersham) was diluted with 14.9991 g unlabelled disulfiram (USP) (Ayerst Laboratories) by stirring for two hours at room temperature in 650 ml reagent grade ethanol (Fisher); 14.9860 g diluted disulfiram was recovered after vacuum drying at 60° C. for 10 days. Two samples of the diluted radiolabeled drug were assayed in triplicate for specific activity on a Beckman LS-100C liquid scintillation counter; the mean specific activity was 336 μCi/g.

A cosolution of C-14 labelled disulfiram and PLGA (1:4 by weight) was prepared in methylene chloride, and cast as a thin film on a clean glass surface. The film was adjusted in thickness to 0.025 inches with a Boston-Bradley film spreader, air dried, then vacuum dried at 45° C. The final dosage form was prepared by extruding rods of this composite through a ⅛ inch die, at a temperature between 70°–80° C. and pressures up to 140 pounds/square inch. These composite rods (20% disulfiram, 80% PLGA) had a mean specific activity of 62.92±8.11 μCi/g.

EXAMPLE 1

Demonstration of Sustained Release of DSF in Animal Studies, Using Two Injected Formulations of DSF: (a) Compounded With PLGA, and (b) Uncompounded Powdered DSF Implantation of Animals Two groups of animals were studied: a test group receiving the subcutaneous C-14-disulfiram-PLGA implant, and a control group receiving subcutaneous uncompounded C-14-disulfiram. Each group comprised five Wistar CD-1 male rats weighing between 100–120 g. After anesthesia with Penthrane (Abbott Laboratories), a slit was cut in the skin of the interscapular region and a small subcutaneous pocket was dissected, large enough for the introduction of the ⅛ inch diameter rods. Each rat received 500 mg of the 20% composite rods (containing 100 mg C-14-disulfiram and 400 mg PLFA) and the wound was closed with clips. The second group of rats served as controls, and received 100 mg of uncompounded powdered C-14-disulfiram in a similar fashion. No attempt was made to preserve strict asepsis during these procedures.

Sample Collection and Analysis

All rats were individually housed in metabolic cages to facilitate the separate collection of urine and feces. Prior to implantation, their fecal and urine samples were collected to determine background counts. Subsequent samples of all excreted urine and feces were collected on days 1,2,7,9,11, 15,18,22,25,29,32,39,46,53,60,67,74,81 and 88 after implantation. Urine samples were assayed for C-14 labelled material in a Beckman LS-230 liquid scintillation counter, and the excretion was calculated as the mass of implanted disulfiram which contained an equivalent amount of radiolabel. Feces were combusted to 14-$CO_2$ with a Harvey Biological oxidizer and absorbed in oxyfluor-$CO_2$ (New England Nuclear) for counting. At the conclusion of the study, the rats were sacrificed and the excised rods from the experimental animals were assayed for residual drug. Pathologic studies were performed on the injection sites of two animals from each group: the sites were inspected for gross changes and tissue sections were prepared (varying from 7μ to 10μ thickness), stained with hematoxylin and eosin, and examined microscopically.

Data Analysis

All data were stored on diskettes using a Radio Shack TRS-80 Model 1 microcomputer (Tandy Corporation, Fort Worth, Tex.) and VisiCalc software (Personal Software Inc, Sunnyvale, Calif.) to calculate the mean and standard deviation of total disulfiram excretion during each collection interval in the test and control groups. The line of best fit for the control group was calculated by the method of least squares.

Drug Excretion

The average daily excretion of radiolabeled material is shown for the test and control groups in FIGS. 1 and 2. The combined excretion in urine and feces is expressed as the mass of implanted disulfiram which originally contained an equivalent amount of radiolabel. In all collection periods, the quantity of radiolabeled material in the urine was approximately ten times greater than the amount detected in the feces. This held true for both groups of animals throughout the duration of the study. The total cumulative recovery of radiolabeled material in urine and feces (expressed as a percentage of the total administered dose ±1 S.D.) was 17.41±2.27% for the group receiving the disulfiram-PLGA composite and 80.54±9.56% for the control group.

Residual Drug in Implanted Composite

The residual radiolabeled material in the excised composite rods accounted for an additional 55.53% (SD=14.83%) of the administered dose of disulfiram. Hence, the total recovery of radiolabel from the rats receiving the PLGA-disulfiram composite accounted for 72.94% (S.D.=14.49%) of the implanted dose. The mean weight of the rods recovered from the implantation sites was 55.53 mg (S.D.=12.84). No residual drug was observed at the injection site in the control group.

Discussion

All excretion of radiolabeled material in this study was expressed in terms of the equivalent quantity of implanted disulfiram. This is not meant to imply that unchanged disulfiram was measured in the urine and feces; to the contrary, there is strong evidence that disulfiram is very rapidly metabolized in the blood and liver, and the breakdown products are promptly excreted. At least one of the metabolites, carbon disulfide, is a volatile compound excreted in the breath, which might account for some part of the discrepancy between the implanted dose and the total amount of drug recovered. The real utility of expressing excretion of radio label in terms of quantity of the drug lies in the insight it provides into the rate of mobilization of the disulfiram from the injection site.

End of Example 1

Preparation of a Sterile Slurry of Disulfiram and Normal Saline

Chemically pure disulfiram USP (Antabuse raw powder) was supplied by Ayerst Laboratories, New York. The drug was manufactured under aseptic conditions in a "clean room" environment, and shipped in a hermetically sealed container. Each unit dose was prepared in a pharmacy under a laminar flow hood, in a clean but not sterile environment. After weighing out 1G disulfiram, the powder was poured into the barrel of a sterile disposable plastic 20 cc syringe from which the plunger had been removed. An occlusive plastic seal on the tip of the syringe prevented any loss of the drug by leakage. The plunger was then replaced in the barrel and depressed to the 10 cc mark. After labelling, the syringe was placed in a Zip-lock ® plastic bag which was then sealed shut, and further sealed with pressure sensitive adhesive tape.

A Best Industries Gammaradiator 100 Cs-137 irradiator was used. The disulfiram unit doses were placed in the 20×20 cm irradiation chamber, 30 cm from a 1800 curie Cesium-137 source emitting 660 KeV gamma rays. The exposure rate at the point of irradiation was 90 R/min. A filter was placed in the beam to ensure a uniform exposure at the floor of the irradiation chamber. A total exposure of 50,000 R was administered. Prior to injection, approximately 10 cc of sterile normal saline was drawn up into the syringe which was then shaken vigorously to suspend the DSF powder. The resultant slurry could then be readily injected through a wide bore (e.g. 14 gauge) needle.

Method for Collecting Breath for the Assay of Acetaldehyde

The method utilizes a Pyrex glass gas-collecting tube (internal volume approximately 300 cc) sealed at both ends with Teflon ® taps. A side-port sealed with a Neoprene rubber septum permits sampling of the contents. The tube is first heated to approximately 70° C. to prevent any condensation from the breath. The subject then blows forcefully into the tube, and the Teflon taps are closed at the end of expiration while the tube is still in the subject's mouth. The tube is then taken to the laboratory, where, after reheating to 70° C., a 2.0 ml sample of the breath is aspirated through the Neoprene septum with a heated syringe and immediately injected into a Gas Chromatograph, for assay of ethanol and acetaldehyde by a standard flame-ionization detection technique. (The method has been described by Phillips et al. in Alcoholism: Clinical & Experimental Research 1984; 8:293-296.)

EXAMPLE 2

Clinical Study of Alcoholic Human Subjects After Injection With DSF-Normal Saline Formulation Two alcoholic human subjects were studied: Subject No.1, a 66 year old black male, and subject No. 2 a 41 year old white female. Each had been through a program of in-patient detoxification from alcohol and had maintained sobriety since discharge while taking an oral dose of disulfiram (250 mg every morning) with no adverse effects. Each was screened with a complete physical examination (to exclude active disease of the liver or other organs) and had a normal chest x-ray, ECG and SMAC 24 (including liver enzymes).

Each subject discontinued oral disulfiram one week before commencing the study. On day zero, each fasted from the preceding midnight, then received a standard alcohol challenge (0.15 G/kg). After eating a meal, and confirming by breath testing (with an Alco-Sensor III) that the blood ethanol concentration had fallen to zero, subject No. 1 received a dose of 1 G disulfiram subcutaneously. The drug was administered in the upper outer quadrant of the right buttock with aseptic precautions using a 14 G needle, after preparing the skin with infiltration of local anesthetic. A control injection of sterile normal saline was administered to the left buttock. Subject No. 2 received 2 G disulfiram in a similar fashion.

A similar alcohol challenge was then repeated on days 7, 14, 21, and 28 after the injection. A physical examination was performed at each visit and the injection site examined.

The following results were obtained.

Injection site—a diminishing subcutaneous lump could be palpated in both subjects during the four weeks of the study. Subject No. 1 experienced no discomfort at the injection site; subject No. 2 experienced some local redness and swelling during the first two days after the injection which then subsided.

Systemic effects—neither subject demonstrated any evidence of skin rash, hepatomegaly, jaundice or peripheral neuropathy during the study. Subject No. 2 noted a taste in her mouth "like dust" during the first week of the study.

Subjective Effects

Subjective responses—the subject was asked to state aloud the number in the following table which most closely accorded with the way he or she felt at the moment. This response was executed every five minutes, following the alcohol challenge, for a two hour period.
1. Very well
2. Alright—no problems
3. A little unwell
4. Very unwell
5. Terrible Clinical Study Subjective effects—Subject No. 1 (1 G disulfiram) experienced no adverse subjective effects following the ethanol challenges during the entire four weeks of the study. However, on day 7, he was noted to be diaphoretic for a 10 minute period, commencing 20 minutes after the ethanol challenge.

Subject No. 2 (2G disulfiram) experienced definite subjective discomfort following the ethanol challenge on day 7; she complained of dizziness, facial flushing, blurred vision and headache, and her conjunctivae were observed to be injected. Her subjective discomfort score rose to 3 ("A little unwell") at 20 and 40 minutes. Similar but progressively less pronounced effects were observed on days 14 and 21, and by day 28, there were no unpleasant symptoms.

Figure 4:
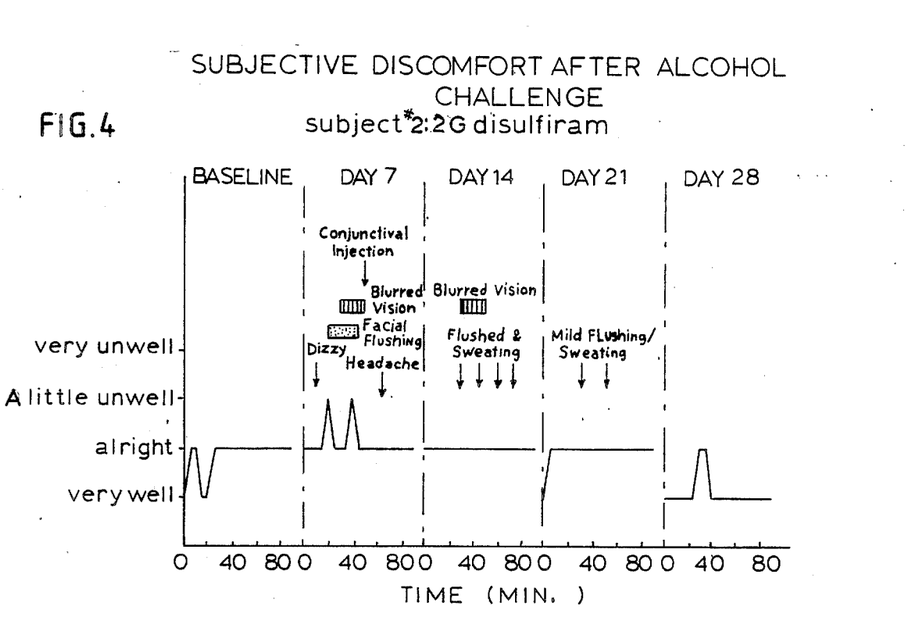
FIG. 4 illustrates the subjective effects following an ethanol challenge in humans injected with disulfiram slurry.

The time course of these subjective effects after alcohol challenge is shown in FIG. 4.

Acetaldehyde Concentration in the Breath

Peak acetaldehyde concentrations (i.e. the highest levels achieved in the breath during the 30-minute period following the ingestion of ethanol) are shown in FIG. 3. When compared to the peak levels observed prior to treatment, the injection of disulfiram induced an elevated peak in Subject No. 1 on day 7, and in Subject No. 2 on days 7 and 14.

Ethanol Concentration in the Breath

Figure 5:
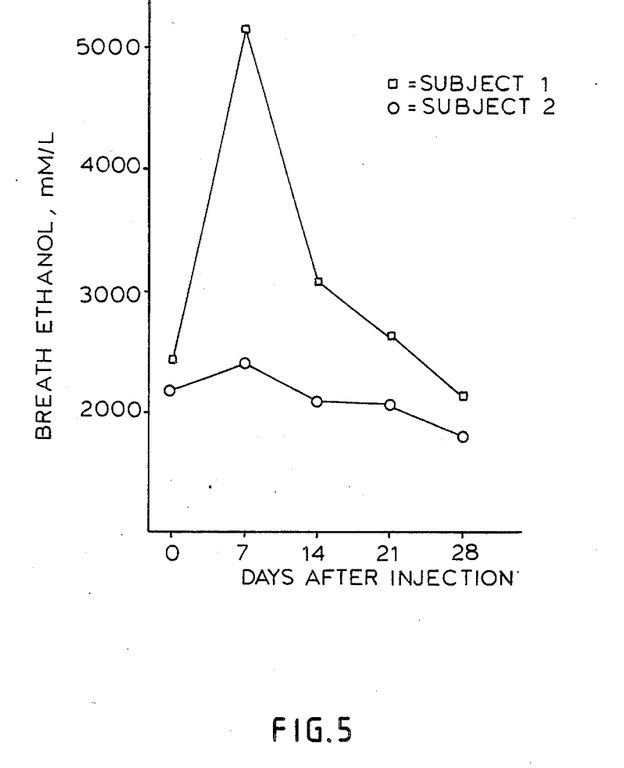
FIG. 5 illustrates ethanol concentrations in breath following an ethanol challenge in humans injected with disulfiram slurry.

Peak ethanol concentrations (i.e. the highest levels achieved in the breath during the 30-minute period following the ingestion of ethanol) are shown in FIG. 5. When compared to the peak levels observed prior to treatment, the injection of DSF induced an elevated peak in subject No. 1, on days 7 and 14, and only a mild elevation in subject No. 2 on day 7.

Elevation in Skin Temperature

Figure 6:
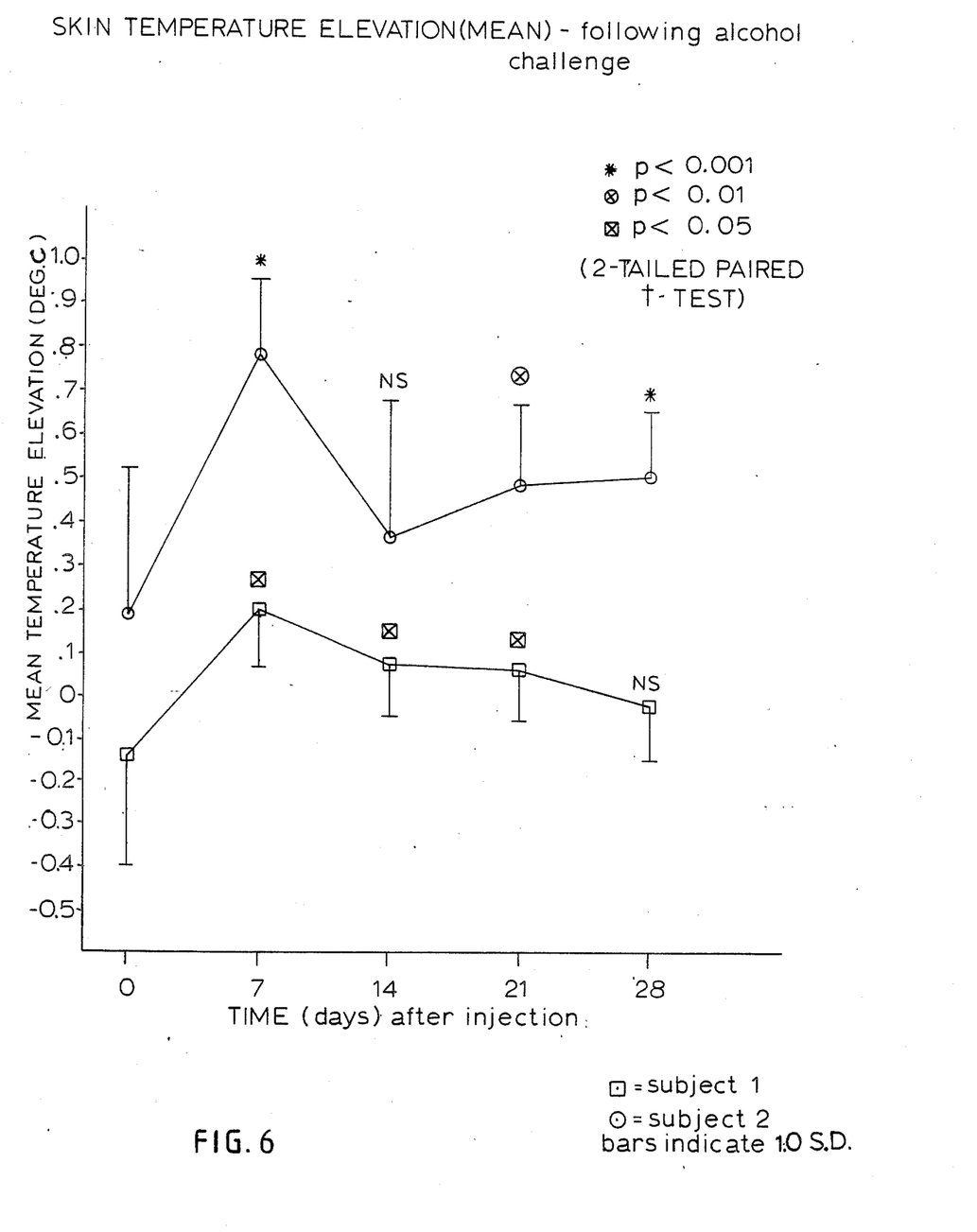
FIG. 6 illustrates elevations in skin temperature following an ethanol challenge in humans injected with disulfiram slurry.

The mean elevations in skin temperature during each 90-minute study are shown in FIG. 6. Bars indicate one standard deviation. NS stands for "not significant."

When compared to the mean elevations observed prior to treatment, dramatic rises were seen in both subjects, peaking at Day 7. Neither subject had returned to the pre-treatment levels by Day 28 of the study. These elevations in mean skin temperature were statistically significant in both subjects (using a paired 2-tailed t-test).

I claim:

1. A process for preparing an injectable composition containing disulfiram as the active ingredient, which comprises; sterilizing the disulfiram with gamma irradiation, and then suspending the sterile disulfiram in sterile normal saline to form a slurry.

2. A method of treating a human suffering from alcoholism, which comprises; injecting said human parenterally, with an effective amount for treatment of disulfiram.

* * * * *